United States Patent [19]

Enders et al.

[11] 4,163,059
[45] Jul. 31, 1979

[54] PESTICIDALLY ACTIVE 4,5-DICHLORO-3-SUBSTITUTED-PHENYLIMINO-1,2-DITHIOLENES

[75] Inventors: Edgar Enders; Ingeborg Hammann; Wilhelm Brandes; Peter Kraus, all of Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 824,940

[22] Filed: Aug. 15, 1977

[30] Foreign Application Priority Data

Aug. 21, 1976 [DE] Fed. Rep. of Germany ....... 2637692
Feb. 19, 1977 [DE] Fed. Rep. of Germany ....... 2707227

[51] Int. Cl.² .................. A61K 31/385; C07D 339/02
[52] U.S. Cl. ..................... 424/277; 424/267; 424/274; 424/248.51; 260/327 C; 260/326.84; 544/145; 546/207
[58] Field of Search .......... 260/327 C, 293.68, 326.84; 544/145; 424/267, 274, 248.51, 277

[56] References Cited

U.S. PATENT DOCUMENTS 3,629,252  12/1971  Bader et al. .................. 260/247.1

FOREIGN PATENT DOCUMENTS 1104893  3/1968  United Kingdom ............... 260/327 C
1126594  1/1972  United Kingdom ............... 260/327 C Primary Examiner—John D. Randolph
Attorney, Agent, or Firm—Sprung, Felfe, Horn, Lynch & Kramer

[57] ABSTRACT 4,5-Dichloro-3-substituted-phenylimino-1,2-dithiolenes of the formula

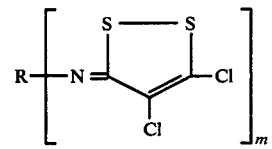

in which R is optionally chlorine-substituted or methoxy-substituted phenyl which carries at least one substituent selected independently from fluorine, bromine, iodine, cyano, thiocyanato, nitro, alkyl, cycloalkyl, halogenoalkyl, aryl, alkoxy with 2–6 carbon atoms, aryloxy, alkylthio, arylthio, acylamino, dialkylamino, alkoxycarbonyl, alkycarbonyl, aminocarbonyl, alkysulphonyl, alkoxysulphonyl, aryloxysulphonyl, aminosulphonyl and N-containing heterocyclic rings, or represents phenyl which is monosubstituted, disubstituted or trisubstituted by chlorine in the 2-, 3-, 2,3-, 2,6-, 3,5-, 2,5-, 3,4,5-, 2,4,6- or 2,4,5-positions, and m is 1 or 2, which possess arthropodicidal, nematicidal and fungicidal properties.

15 Claims, No Drawings

PESTICIDALLY ACTIVE 4,5-DICHLORO-3-SUBSTITUTED-PHENYLIMINO-1,2-DITHIOLENES

The present invention relates to and has for its objects the provision of particular new 4,5-dichloro-3-substituted-phenylimino-1,2-dithiolenes which possess pesticidal properties, active compositions in the form of mixtures of such compounds with solid and liquid dispersible carrier vehicles, and methods for producing such compounds and for using such compounds in a new way especially for combating pests, e.g. arthropods, nematodes and fungi, with other and further objects becoming apparent from a study of the within specification and accompanying examples.

Pesticides in this context are to be understood as agents which permit the combating of animal pests and phytopathogenic fungi in locations where they are not desired.

3-Arylimino-4,5-dichloro-1,2-dithiols, such as, for example, 4-chlorophenylimino-(Compound A) and 2,4- (Compound B) and 3,4-dichloro-phenylimino-4,5-dichloro-1,2-dithiol (Compound C), have already been disclosed. These compounds are suitable for combating phyto-pathogenic fungi, but their action is not always entirely satisfactory if low concentrations are used.

The present invention now provides, as new compounds, the 4,5-dichloro-3-arylimino-1,2-dithiolenes of the general formula

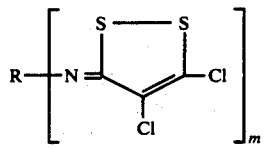

in which
R represents optionally chlorine-substituted or methoxy-substituted phenyl, which carries one or more substituents selected independently from fluorine, bromine, iodine, cyano, thiocyananto, nitro, alkyl, cycloalkyl, halogenoalkyl, aryl, alkoxy with 2–6 carbon atoms, aryloxy, alkylthio, arylthio, acylamino, dialkylamino, alkoxycarbonyl, alkycarbonyl, aminocarbonyl, alkylsulphonyl, alkoxysulphonyl, aryloxysulphonyl, aminosulphonyl and N-containing heterocyclic rings, or represents phenyl which is monosubstituted, disubstituted or trisubstituted by chlorine in the 2-, 3-, 2,3-, 2,6-,3,5-, 2,5-, 3,4,5-, 2,4,6- or 2,4,5-positions, and
m represents 1 or 2.

The compounds of the formula (I) have been found to possess powerful arthropodicidal, nematicidal, fungicidal and ectoparasiticidal properties.

Preferably, R represents phenyl which is optionally substituted by chlorine or methoxy and which carries one or more substituents selected independently from bromine, fluorine, iodine, cyano, nitro, thiocyanato, $C_{1-6}$-alkyl, cyclopentyl, cyclohexyl, $C_{1-4}$ halogenoalkyl with up to 3 halogen atoms, phenyl, $C_{2-6}$-alkoxy, optionally substituted phenoxy, $C_{1-6}$-alkylthio, optionally substituted phenylthio, $C_{1-6}$-acylamino, $C_{1-4}$-dialkylamino, piperidino, $C_{1-6}$-alkoxycarbonyl, $C_{1-6}$-alkylcarbonyl, aminocarbonyl, $C_{1-4}$-dialkylaminocarbonyl, $C_{1-6}$-alkylsulphonyl, $C_{1-6}$-alkoxysulphonyl, optionally substituted phenoxysulphonyl, aminosulphonyl, $C_{1-4}$-dialkylaminosulphonyl, pyrrolidinosulphonyl and morpholinosulphonyl, or represents phenyl which is substituted by chlorine in the 2-, 3-, 2,6-, 3,5-, 2,5-, 3,4,5-, 2,4,6- or 2,4,5-positions.

Particularly preferred compounds are those in which R represents phenyl which is optionally substituted by chlorine or methoxy and which carries one or more substituents selected independently from bromine, methyl, ethyl, n-propyl, i-propyl, sec.-butyl, i-butyl, t-butyl, t-pentyl, 2-hexyl, cyclopentyl, cyclohexyl, phenyl, trifluoromethyl, ethoxy, isopropoxy, butoxy, hexyloxy, phenoxy, 4-chlorophenoxy, 4-nitrophenoxy, 2,4-dichlorophenoxy, 4-aminophenoxy, methylthio, ethylthio, butylthio, phenylthio, 4-chlorophenylthio, 4-chlorophenylthio, 4-aminophenylthio, nitro, acetylamino, butyrylamino, benzoylamino, dimethylamino, diethylamino, dibutylamino, piperidine, methoxycarbonyl, ethoxycarbonyl, butoxycarbonyl, hexylcarbonyl, aminocarbonyl, dimethylaminocarbonyl, diethylaminocarbonyl, dibutylaminocarbonyl, methylsulphonyl, methoxysulphonyl, ethoxysulphonyl, butoxysulphonyl, hexyloxysulphonyl, isopropoxysulphonyl, phenoxysulphonyl, aminosulphonyl, dimethylaminosulphonyl, diethylaminosulphonyl, pyrrolidinosulphonyl and morpholinosulphonyl.

Another preferred class of compounds is represented by the general formula

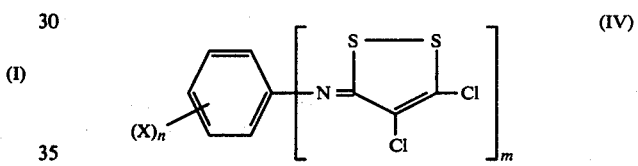

in which
m represents 1 or 2,
n represents 1, 2 or 3 and
X represents cyano, thiocyanato, nitro, alkyl, cycloalkyl, halogenoalkyl, aryl, alkoxy with 2–6 carbon atoms, aryloxy, alkylthio, arylthio, acylamino, dialkylamino, alkoxycarbonyl, alkylcarbonyl, aminocarbonyl, alkylsulphonyl, alkoxysulphonyl, aryloxysulphonyl, aminosulphonyl or a N-containing heterocyclic ring, or, provided m represents 1, $(X)_n$ represents chlorine substituents in the 2-, 2,3-, 2,6-, 3,5- or 3,4,5-positions.

The present invention also provides a process for the preparation of a 4,5-dichloro-3-arylimino-1,2-dithiolene of the formula (I) in which an aromatic amine of the general formula $$R\text{\textendash}NH_2]_m \qquad (II)$$

wherein
R and m have the above-mentioned meanings, is reacted with 3,4,5-trichloro-1,2-dithiolium chloride (3,4,5,5-tetrachloro-1,2-dithiolene), which may be represented by the formulae

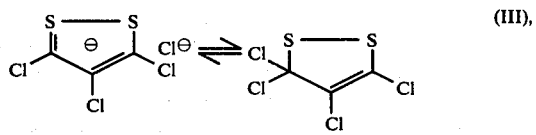

if appropriate in an inert solvent, in the presence of an acid-binding agent.

If 3,5-dichloro-aniline is reacted with 3,4,5-trichloro-1,2-dithiolium chloride to give 4,5-dichloro-3-(3,5-dichlorophenylimino)-1,2-dithiolene, the course of the reaction can be represented by the following equation:

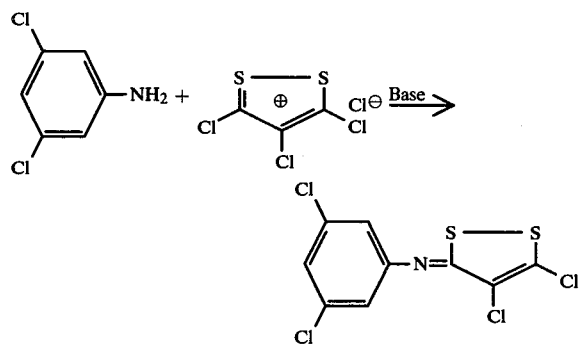

The following may be mentioned as examples of compounds of the general formula (II) which can be used for the preparation of the compounds according to the invention: 2- or 3-chloro-aniline, 4-fluoroaniline, 2- and 4-bromoaniline, 4-iodo-aniline, 2,3-, 2,5-, 2,6- and 3,5-dichloro-aniline, 2,4,5-, 3,4,5- and 2,4,6-trichloro-aniline, 2-chloro-4-fluoroaniline, 2-chloro-4-bromo-aniline, 2-bromo-4-chloro-aniline, 4-bromo-4-chloro-aniline, 4-bromo-2,5-dichloro-aniline, 2-, 3- and 4-methyl-aniline, 2,4-, 2,3-, 2,5-, 2,6-, 3,4- and 3,5-dimethylaniline, 2,3,4-, 2,4,5- and 2,4,6-trimethyl-aniline, 2- and 4-ethyl-aniline, 2,6-diethyl-aniline, 2- and 4-isopropylaniline, 2,6-diisopropylaniline, 2-sec.-butyl-aniline, 4-isobutyl-aniline, 4-tert.-butylaniline, 4-methyl-2,6-diethylaniline, 2-methyl-4-tert.-butyl-aniline, 2-cyclopentyl-aniline, 2-cyclohexyl-aniline, 4-chloro-2-methyl-aniline, 4-chloro-2,5-dimethylaniline, 2-chloro-4-methyl-aniline, 4-bromo-2-methyl-aniline, 4-bromo-2-ethyl-aniline, 4-amino-biphenyl, 2-amino-biphenyl, 4-amino-4'-chloro-biphenyl, 2- or 3-methoxyaniline, 2- and 4-ethoxy-aniline, 2,4- and 2,5-dimethoxy-aniline, 3,4,5-trimethoxy-aniline, 4-chloro-2,5-dimethoxy-aniline, 4-methyl-2,5-dimethoxy-aniline, 2,5-diethoxy-aniline, 4-butoxy-aniline, 4-hexyloxy-aniline, 4-amino-diphenyl ether, 4-chloro-4'-amino-diphenyl ether, 4,4'-diamino-diphenyl ether, 2-amino-diphenyl ether, 2-amino-4'-methyl-diphenyl ether, 2-amino-2'-nitro-diphenyl ether, 2- and 4-methylthio-aniline, 4-butylthio-aniline, 2-hexylthio-aniline, 4-amino-diphenyl sulphide, 2-amino-4-chlorodiphenyl sulphide, 2-, 3- and 4-nitro-aniline, 2-methyl-4-nitro-aniline, 2-chloro-4-nitro-aniline, 2-methoxy-4-nitro-aniline, 3-nitro-6-chloro-aniline, 3-nitro-6-methyl-aniline, 2-, 3- and 4-acetylamino-aniline, 3-butyrylamino-aniline, 4-benzoylamino-aniline, 4-acetylamino-2-methyl-aniline, 4-acetylamino-3-methyl-aniline, 3-nitro-4-acetylaminoaniline, 2-chloro-5-acetylamino-aniline, 2-, 3- and 4-dimethylamino-aniline, 3-chloro-4-dimethylamino-aniline, 4-methyl-3-dimethylamino-aniline, 4-diethylamino-aniline, 4-dibutylamino-aniline, 4-piperidino-aniline, 2,4-bisdimethylamino-aniline, 2-, 3- and 4-amino-benzonitrile, 4-chloro-3-amino-benzonitrile, 4-methoxy-3-amino-benzonitrile, 3,5-dicyano-aniline, anthranilic acid methyl ester, ethyl ester and butyl ester, 3-amino-benzoic acid methyl ester and butyl ester, 4-amino-benzoic acid ethyl ester and hexyl ester, 4-chloro-anthranilic acid methyl ester, 5-nitroanthranilic acid ethyl ester, 4-chloro-3-amino-benzoic acid methyl ester, 3-chloro-4-amino-benzoic acid methyl ester, anthranilic acid dimethylamide, anthranilic acid dibutylamide, 3-aminobenzoic acid dimethylamide, 4-amino-benzoic acid amide, 4-aminobenzenesulphonic acid methyl ester, 4-amino-benzenesulphonic acid butyl ester, 3-amino-benzenesulphonic acid methyl ester, 3-amino-benzenesulphonic acid ethyl ester, 3-amino-benzenesulphonic acid hexyl ester, 2-amino-benzenesulphonic acid cyclohexyl ester, 3-amino-4-chloro-benzenesulphonic acid isopropyl ester, 4-amino-3-methyl-benzenesulphonic acid butyl ester, 2-amino-benzenesulphonic acid dimethylamide, 3-amino-benzenesulphonic acid diethylamide, 4-amino-benzenesulphonic acid pyrrolidide, 2-amino-5-chloro-benzenesulphonic acid dimethylamide, 3-amino-4-chloro-benzenesulphonic acid amide, 4-amino-2-methyl-benzenesulphonic acid morpholide, 1,4-diamino-benzene, 1,3-diamino-benzene, 3-chloro-1,4-diamino-benzene, 3,5-dichloro-1,4-diamino-benzene, 4-chloro-1,3-diamino-benzene, 4-methyl-1,4-diamino-benzene, 4,4'-diamino-diphenyl ether, 2,4'-diamino-diphenyl ether, 2,2'-diamino-diphenyl ether, 5-chloro-2,4'-diamino-diphenyl ether, 2,4-diamino-diphenyl ether, 4'-chloro-2,4-diamino-diphenyl ether, 4,4'-diamino-diphenyl sulphide, 4,4'-diamino-diphenyl sulphone, 4-amino-benzenesulphonic acid 4'-amino-phenyl ester and 3-amino-benzoic acid 3'-amino-anilide.

The compounds of the general formula (II) are known and can be prepared in accordance with known methods.

3,4,5-Trichloro-1,2-dithiolium chloride (3,4,5,5-tetrachloro-1,2-dithiolene), used for the reaction, is also known (Angew. Chemie 72, 629 (1960)).

The reaction of the compounds (II) with 3,4,5-trichloro-1,2-dithiolium chloride is preferably carried out in equivalent or approximately equivalent ratios, in an inert solvent, with addition of an acid-binding agent. Advantageously, a slight excess of 3,4,5-trichloro-1,2-dithiolium chloride (for example 10–20% of theory) is used. Preferred inert solvents are those which are capable of dissolving or partially dissolving the 3,4,5-trichloro-1,2-dithiolium chloride. The following may be mentioned as examples of suitable solvents: halogenohydrocarbons such as methylene chloride, chloroform, carbon tetrachloride, dichloroethane, trichloroethylene, tetrachloroethylene and chlorobenzene, as well as aromatic hydrocarbons such as benzene, toluene and xylene. Further suitable solvents are ethers, such as 1,2-dimethoxyethane, dioxane, tetrahydrofuran and diisopropyl ether, and other polar solvents such as acetonitrile, dimethylformamide and N-methyl-pyrrolidone.

The reaction in general takes place at an adequate speed at room temperature, but if necessary the mixture can be warmed, for example up to the boiling point of the solvent used, for example to 50°–120° C. The reaction takes place with the elimination of 2 moles of hydrogen chloride per NH$_2$ equivalent. To bind the hydrogen chloride, a slight excess of an acid-binding agent, preferably of a tertiary organic base, is used. Suitable bases which may be mentioned are trimethylamine, triethylamine, diisopropylamine, 1,4-diazabicyclo-(2,2,2)-octane (DABCO), 1,5-diaza-bicyclo-(4,3,0)-non-5-ene (DBN) and 2,8-diaza-bicyclo-(5,4,0)-undec-7-ene (DBU).

However, it is also possible, when using a suitable method (two-phase system, low temperature), to employ inorganic bases, for example an alkali metal hydroxide solution, a concentrated suspension of sodium bicarbonate, sodium carbonate, potassium carbonate, trisodium phosphate or basic metal oxides such as magnesium oxide, calcium oxide and zinc oxide.

The course of the reaction can easily be followed by carrying out a test for aromatic amine (diazotization and coupling reaction). After complete reaction, solutions of the reaction product in the solvent used are generally obtained, from which the acid-binding agent can be washed out by means of water, if appropriate with addition of dilute acid.

Where water-soluble solvents are concerned, the reaction product can usually be filtered off directly after dilution with water. Oily reaction products are advantageously isolated from water-insoluble solvents (chlorohydrocarbons) by washing, drying, chromatographing over an aluminum oxide column, and evaporating.

The pure 4,5-dichloro-3-arylimino-1,2-dithiolenes form pale-colored viscous oils or low-melting crystals.

The following may be mentioned as examples of the compounds which can be prepared according to the invention: 4,5-dichloro-3-(4-chloro-2-trifluoromethyl-phenylimino)-1,2-dithiolene, 4,5-dichloro-3-(2-chloro-5-trifluoromethylphenylimino)-1,2-dithiolene, 4,5-dichloro-3-(3,5-bis-trifluoromethyl-phenylimino)-1,2-dithiolene, 4,5-dichloro-3-(4-chloro-2-methyl-phenylimino)-1,2-dithiolene, 4,5-dichloro-3-(2,4,5-trichloro-phenylimino)-1,2-dithiolene, 4,5-dichloro-3-(3,5-dichloro-phenylimino)-1,2-dithiolene, 4,5-dichloro-3-(2,6-dichloro-phenylimino)-1,2-dithiolene, 4,5-dichloro-3-(2,3-dichloro-phenylimino)-1,2-dithiolene, 4,5-dichloro-3-(2-chloro-phenylimino)-1,2-dithiolene, 4,5-dichloro-3-(2,6-diethyl-phenylimino)-1,2-dithiolene, 4,5-dichloro-3-(2,6-diisopropyl-phenylimino)-1,2-dithiolene, 4,5-dichloro-3-(2,5-dimethoxy-phenylimino)-1,2-dithiolene, 4,5-dichloro-3-(2,5-dichloro-phenylimino)-1,2-dithiolene, 4,5-dichloro-3-(2-chloro-4-fluoro-phenylimino)-1,2-dithiolene, 4,5-dichloro-3-(2-chloro-4-bromo-phenylimino)-1,2-dithiolene, 4,5-dichloro-3-(2-bromo-4-chloro-phenylimino)-1,2-dithiolene, 4,5-dichloro-3-(2,4-dibromo-phenylimino)-1,2-dithiolene, 4,5-dichloro-3-(4-iodo-phenylimino)-1,2-dithiolene, 4,5-dichloro-3-(4-bromo-2,5-dichloro-phenylimino)-1,2-dithiolene, 4,5-dichloro-3-(4-methyl-2,5-dichloro-phenylimino)-1,2-dithiolene, 4,5-dichloro-3-(5-methyl-2,4-dichloro-phenylimino)-1,2-dithiolene, 4,5-dichloro-3-(2-methyl-phenylimino)-1,2-dithiolene, 4,5-dichloro-3-(3-methyl-phenylimino)-1,2-dithiolene, 4,5-dichloro-3-(4-methyl-phenylimino)-1,2-dithiolene, 4,5-dichloro-3-(2,3-dimethyl-phenylimino)-1,2-dithiolene, 4,5-dichloro-3-(2,6-dimethyl-phenylimino)-1,2-dithiolene, 4,5-dichloro-3-(3,4-dimethyl-phenylimino)-1,2-dithiolene, 4,5-dichloro-3-(3,5-dimethyl-phenylimino)-1,2-dithiolene, 4,5-dichloro-3-(2,5-dimethyl-phenylimino)-1,2-dithiolene, 4,5-dichloro-3-(2,4,5-trimethyl-phenylimino)-1,2-dithiolene, 4,5-dichloro-3-(2,4,6-trimethyl-phenylimino)-1,2-dithiolene, 4,5-dichloro-3-(2-ethyl-phenylimino)-1,2-dithiolene, 4,5-dichloro-3-(2,4-diethyl-phenylimino)-1,2-dithiolene, 4,5-dichloro-3-(4-isopropyl-phenylimino)-1,2-dithiolene, 4,5-dichloro-3-(4-tert.-butyl-phenylimino)-1,2-dithiolene, 4,5-dichloro-3-(4-cyclohexyl-phenylimino)-1,2-dithiolene, 4,5-dichloro-3-(2-cyclohexyl-phenylimino)-1,2-dithiolene, 4,5-dichloro-3-(4-bromo-2-ethyl-phenylimino)-1,2-dithiolene, 4,5-dichloro-3-(1-biphenylyl-imino)-1,2-dithiolene, 4,5-dichloro-3-(2-ethoxy-phenylimino)-1,2-dithiolene, 4,5-dichloro-3-(2,4-dimethoxy-phenylimino)-1,2-dithiolene, 4,5-dichloro-3-(4-butoxy-phenylimino)-1,2-dithiolene, 4,5-dichloro-3-(4-hexyloxy-phenylimino)-1,2-dithiolene, 4,5-dichloro-3-(methylsulphonylphenylimino)-1,2-dithiolene, 4,5-dichloro-3-(4-chloro-2,5-dimethoxy-phenylimino)-1,2-dithiolene, 4,5-dichloro-3-(2-phenoxy-phenylimino)-1,2-dithiolene, 4,5-dichloro-3-(3-(2-chloro-phenoxy)-phenylmino)-1,2-dithiolene, 4,5-dichloro-3-(2-chloro-4-methylthio-phenylimino)-1,2-dithiolene, 4,5-dichloro-3-(2-chloro-4-methylsulphonylphenylimino)-1,2-dithiolene, 4,5-dichloro-3-(4-butylthiophenylimino)-1,2-dithiolene, 4,5-dichloro-3-(2-phenylthiophenylimino)-1,2-dithiolene, 4,5-dichloro-3-(5-chloro-2-phenylthio-phenylimino)-1,2-dithiolene, 4,5-dichloro-3-(2-nitro-phenylimino)-1,2-dithiolene, 4,5-dichloro-3-(3-nitro-phenylimino)-1,2,-dithiolene, 4,5-dichloro-3-(4-nitro-phenylimino)-1,2-dithiolene, 4,5-dichloro-3-(2-chloro-5-nitrophenylimino)-1,2-dithiolene, 4,5-dichloro-3-(2,4-dichloro-5-nitro-phenylimino)-1,2-dithiolene, 4,5-dichloro-3-(2,4-dimethyl-5-nitro-phenylimino)-1,2-dithiolene, 4,5-dichloro-3-(3-acetylamino-phenylimino)-1,2-dithiolene, 4,5-dichloro-3-(4-chloro-3-isobutyrylamino-phenylimino)-1,2-dithiolene, 4,5-dichloro-3-(4-dimethylamino-phenylimino)-1,2-dithiolene, 4,5-dichloro-3-(4-chloro-4-dimethylamino-phenylimino)-1,2-dithiolene, 4,5-dichloro-3-(4-piperidino-phenylimino)-1,2-dithiolene, 4,5-dichloro-3-(2-chloro-4-cyano-phenylimino)-1,2-dithiolene, 4,5-dichloro-3-(2-chloro-4-methoxycarbonylphenylimino)-1,2-dithiolene, 4,5-dichloro-3-(2-chloro-4-dimethylaminocarbonyl-phenylimino)-1,2-dithiolene, 4,5-dichloro-3-(2-chloro-4-phenoxysulphonyl-phenylimino)-1,2-dithiolene, 4,5-dichlor-3-(2-chloro-4-phenoxysulphonyl-phenylimino)-1,2-dithiolene, 4,5-dichloro-3-(2-methyl-5-dimethylaminosulphonyl-phenylimino)-1,2-dithiolene, N,N'-bis-(4,5-dichloro-1,2-dithiolen-3-ylidene)-1,4-phenylenediamine, N,N'-bis-(4,5-dichloro-1,2-dithiolen-3-ylidene)-1,3-phenylenediamine, N,N'-bis-(4,5-dichloro-1,2-dithiolen-3-ylidene)-4-chloro-1,3-phenylenediamine, N,N'-bis-(4,5-dichloro-1,2-dithiolen-3-ylidene)-4-methyl-1,3-phenylenediamine, N,N'-bis-(4,5-dichloro-1,2-dithiolene-3-ylidene)-4-phenoxy-1,3-phenylenediamine, N,N'-bis-(4,5-dichloro-1,2-dithiolen-3-ylidene)-4-phenylthio-1,3-phenylenediamine, N,N'-bis-(4,5-dichloro-1,2-dithiolene-3-ylidene)-4,4'-diaminodiphenyl ether, N,N'-bis-(4,5-dichloro-1,2-dithiolen-3-ylidene)-4,2'-diaminodiphenyl ether and N,N'-bis-(4,5-dichloro-1,2-dithiolen-3-ylidene)-3-amino-benzenesulphonic acid 3'-amino-phenyl ester.

The active compounds are well tolerated by plants, have a favorable level of toxicity to warm-blooded animals, and can be used for combating arthropod pests, especially insects and arachnids, and nematodes, which are encountered in agriculture, in forestry, in the protection of stored products and of materials, and in the hygiene field and the veterinary field. They are active against normally sensitive and resistant species and against all or some stages of development. The above-mentioned pests include:

from the class of the Isopoda, for example, *Oniscus asellus, Armadillidium vulgare* and *Porcellio scaber;* from the class of the *Diplopoda*, for example *Blaniulus guttulatus;* from the class of the *Chilopoda*, for example *Geophilus carpophagus* and *Scutigera* spec.; from the class of the *Symphyla*, for example, *Scutigerella immaculata;* from the order of the *Thysanura*, for example *Lepisma saccharina;* from the order of the *Collembola*, for example *Onychiurus armatus;* from the order of the *Orthoptera,* for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the *Dermaptera,* for example *Forficula auricularia;* from the order of the *Isoptera,* for example *Reticulitermes* spp.; from the order of the *Anoplura,* for example *Phylloxera vastatrix, Pemphigus* spp., *Pediculus humanus corporis, Haematopinus* spp. and *Linognathus* spp.; from the order of the *Mallophaga,* for example *Trichodectes* spp. and *Damalinea* spp.; from the order of the *Thysanoptera,* for example *Hercinothrips femoralis* and *Thrips tabaci;* from the order of the *Heteroptera,* for example *Eurygaster* spp., *Dysdercus intermedius, Piesma quadrata, Cimex lectularius, Rhodnius prolixus* and *Triatoma* spp.; from the order of the *Homoptera,* for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.; from the order of the *Lepidoptera,* for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Laphygma exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the *Coleoptera,* for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica;* from the order of the *Hymenoptera,* for example *Diprion* spp., *Hoplocampa* spp., *Lasius* spp., *Monomorium pharaonis* and *Vespa* spp.; from the order of the *Diptera,* for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa;* from the order of the *Siphonaptera,* for example *Xenopsylla cheopis* and *Ceratophyllus* spp.; from the class of the *Arachnida,* for example *Scorpio maurus* and *Latrodectus mactans;* from the order of the *Acarina,* for example *Acarus siro, Argas* spp., *Ornithodoros* spp., *Dermanyssus gallinea, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp..

The plant-parasitic nematodes include *Pratylenchus* spp., *Radopholus similis, Ditylenchus dipsaci, Tylenchulus semipenetrans, Heterodera* spp., *Meloidogyne* spp., *Aphelenchoides* spp., *Longidorus* spp., *Xiphinema* spp. and *Trichodorus* spp.

The active compounds according to the invention also exhibit a powerful fungitoxic action. They do not damage crop plants in the concentrations required for combating fungi. For these reasons, they are suitable for use as plant protection agents for combating fungi. Fungitoxic agents are employed in plant protection for combating *Plasmodiophoromycetes, Oomycetes, Chytridiomycetes, Zygomycetes, Ascomycetes, Basidiomycetes* and *Deuteromycetes.*

The active compounds according to the invention have a broad spectrum of action and can be used against parasitic fungi which attack above-ground parts of plants or attack the plants through the soil, as well as against seed-borne pathogens.

The active compounds according to the invention exhibit a particularly good activity against parasitic fungi which attack above-ground parts of plants, such as rust diseases of cereals, caused by species of *Puccinia,* and bean rust (*Uromyces phaseoli*), and also against powdery mildew caused by species of *Erysiphe,* and powdery mildew of apples (*Podosphaera leucotricha*) and, in the case of rice, against *Pyricularia oryzae* and *Pellicularia sasakii.* On above-ground parts of plants, the compounds are also active against species of *Botrytis,* species of *Septoria,* species of *Helminthosporium* and species of *Cercospora.* The active compounds according to the invention are effective, and of particular practical importance, if they are employed as seed dressings or soil treatment agents against phytopathogenic fungi which adhere to the seed and occur in the soil, and cause seedling diseases, root rots, tracheomycoses and seed diseases of crop plants, such as species of *Fusarium,* species of *Rhizoctonia, Verticillium alboatrum* and *Phialophora cinerescens.*

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichlorofluoromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, nematicides and fungicides, or bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, nematodes and fungi, which comprises applying to at least one of correspondingly (a) such arthropods, (b) such nematodes, (c) such fungi, and (d) the corresponding habitat thereof, i.e., the locus to be protected, e.g. to a growing crop, to an area where a crop is to be grown or to a domestic animal, a correspondingly combative or toxic amount, i.e., an arthropodicidally, nematicidally or fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all the spider mites were killed whereas 0% meant that none of the spider mites were killed.

The active compounds, the concentrations of the active compounds, the evaluation times and the results can be seen from the following table:

Table 1
(Mites which damage plants)
*Tetrahychus* test

| Active compounds | Active compound concentration in % | Degree of destruction in % after 2 days |
|---|---|---|
| 4-Cl-C₆H₄ derivative (A) (known) | 0.1 / 0.01 | 99 / 0 |
| 3,4-Cl₂-C₆H₃ derivative (C) (known) | 0.1 / 0.01 | 55 / 0 |
| 2,4-(CH₃)₂-C₆H₃ derivative (9) | 0.1 / 0.01 | 100 / 100 |
| 3,5-(CF₃)₂-C₆H₃ derivative (4) | 0.1 / 0.01 | 100 / 90 |
| 2-Cl-5-CF₃-C₆H₃ derivative (3) | 0.1 / 0.01 | 99 / 90 |
| 2-Cl-C₆H₄ derivative (10) | 0.1 / 0.01 | 100 / 50 |
| 2,3-Cl₂-C₆H₃ derivative (8) | 0.1 / 0.01 | 100 / 95 |
| 3,5-Cl₂-C₆H₃ derivative (1) | 0.1 / 0.01 | 98 / 95 |
| 2,4,5-Cl₃-C₆H₂ derivative (6) | 0.1 / 0.01 | 100 / 99 |

EXAMPLE 2

Drosophila test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 cm³ of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all the flies were killed; 0% meant that no flies were killed.

The active compounds, the concentrations of the active compounds, the evaluation times and the results can be seen from the following table:

Table 2
(Insects which damage plants)
Drosphila test

| Active compounds | Active compound concentration in % | Degree of destruction in % after 1 day |
|---|---|---|
| [structure (4): 3,5-bis(CF$_3$)-phenyl-N=C(S-S-CCl=CCl-)] | 0.1 | 100 |
| [structure (3): 2-Cl-5-CF$_3$-phenyl-N=C(S-S-CCl=CCl-)] | 0.1 | 80 |
| [structure (14): bis-dithiole phenylenediimine] | 0.1 | 80 |

EXAMPLE 3

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18°–20° C. and at a relative atmospheric humidity of 100%.

The plants were then brought into a greenhouse for 14 days.

15 days after inoculation, the infection of the seedlings was determined. The ratings obtained were converted to percent infection. 0% meant no infection; 100% meant that the plants were completely infected.

The active compounds, the concentrations of the active compounds and the results can be seen from the following table:

Table 3
Fusicladium test (apple)/protective

| Active compound | Infection in % at an active compound concentration of 0.0005% |
|---|---|
| [3,4-diCl-phenyl derivative] (known) (C) | 29 |
| [2,4-diCl-phenyl derivative] (known) (C) | 24 |
| [2-CH$_3$-4-Cl-phenyl derivative] (5) | 1 |
| [2,4-diCl-phenyl derivative] (1) | 1 |
| [2-Cl-phenyl derivative] (10) | 4 |

Table 3-continued

Fusicladium test (apple)/protective

| Active compound | Infection in % at an active compound concentration of 0.0005% |
|---|---|
| 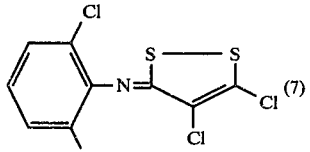 (7) | 1 |
| 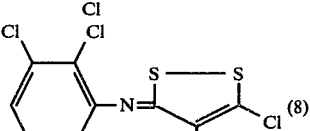 (8) | 0 |

EXAMPLE 4

Fusicladium test (apple scab)/Curative

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4-6 leaf stage were inoculated with an aqueous conidium suspension of the apple scab causative organism (*Fusicladium dendriticum*) and incubated for 18 hours in a humidity chamber at 18°-20° C. and at a relative atmospheric humidity of 100%. The plants were then brought into a greenhouse and allowed to dry.

After standing for a suitable period of time, the plants were sprayed dripping wet with the spray liquid prepared in the manner described above. The plants were then again brought into a greenhouse.

15 days after inoculation, the infection of the apple seedlings was determined as a percentage of the untreated but also inoculated control plants.

0% meant no infection; 100% meant that the infection was exactly as great as in the case of the control plants.

The active compounds, the concentrations of the active compounds, the period of time between inoculation and spraying and the results obtained can be seen from the following table:

Table 4

Fusicladium test (apple)/curative

| Active compound | Residence time in hours | Infection in % at an active compound concentration of 0.01% |
|---|---|---|
| 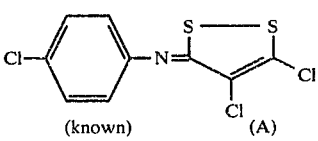 (known) (A) | 42 | 61 |

Table 4-continued

Fusicladium test (apple)/curative

| Active compound | Residence time in hours | Infection in % at an active compound concentration of 0.01% |
|---|---|---|
| 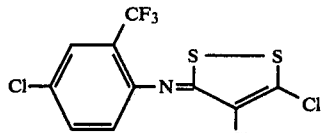 (2) | 42 | 19 |
| 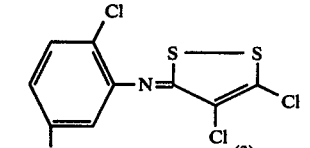 (3) | 42 | 35 |
| 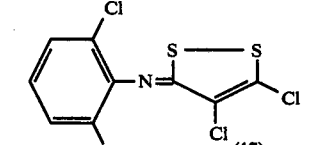 (17) | 42 | 35 |

EXAMPLE 5

Scab mite test 10-25 specimens, at various stages of development, of the rabbit ear mite (*Psoroptes cuniculi*) were introduced into filterpaper sandwiches which were impregnated with an active compound solution of the stated concentration. After 24 hours, the action was examined and quoted in %. 100% meant that all mites had been killed and 0% meant that none of the mites had been killed.

Table 5

Scab mite test (*Psoroptes cuniculi*)

| Active compound | Active compound concentration in ppm | Destructive action in % in 24 hours |
|---|---|---|
| Compound (5): 4-Cl, 2-CH₃ phenyl-N=C(S-S)C(Cl)=C(Cl) [2-methyl-4-chloro-phenylimino dithiolene] | 100<br>30 | 100<br>100 |
| Compound (3): 2-Cl, 5-CF₃ phenyl analog | 100<br>30 | 100<br>100 |
| Compound (4): 3,5-bis-CF₃ phenyl analog | 100<br>30 | 100<br>100 |
| Compound (1): 3,5-dichloro-phenyl analog | 100 | 100 |
| Compound (12): 2,6-diisopropyl-phenyl analog | 100<br>30 | 100<br>100 |

The process of the present invention is illustrated by the following preparative examples:

EXAMPLE 6 (Compound 1)

4,5-Dichloro-3-(3,5-dichloro-phenylimino)-1,2-dithiolene 18.5 g of 3,5-dichloro-aniline were dissolved in 300 ml of methylene chloride and 50 ml of triethylamine and 31.0 g of 3,4,5-trichloro-1,2-dithiolium chloride were introduced at 10°–15° C. The mixture was stirred for about 12 hours, until a test for aromatic amine, by diazotizing and coupling, proved negative. The resulting dark solution was then washed three times with 200 ml of water, dried over potassium carbonate and filtered over a column of aluminum oxide, to remove impurities that imparted a color. The filtrate was reduced to dryness in vacuo and the residue was recrystallized from petroleum ether.

Yield 20.0 g; melting point: 107°–108° C.

The elementary analysis and NMR spectrum agreed with the assumed structure.

The following were obtained analogously:

Compound 2

4,5-Dichloro-3-(4-chloro-2-trifluoromethyl-phenylimino)-1,2-dithiolene (viscous oil).

Compound 3

4,5-Dichloro-3-(2-chloro-5-trifluoromethyl-phenylimino)-1,2-dithiolene (viscous oil).

Compound 4

4,5-Dichloro-3-(3,5-bis-trifluoromethyl-phenylimino)-1,2-dithiolene (viscous oil).

Compound 5

4,5-Dichloro-3-(4-chloro-2-methyl-phenylimino)-1,2-dithiolene; melting point: 106°–108° C.

Compound 6

4,5-Dichloro-3-(2,4,5-trichloro-phenylimino)-1,2-dithiolene; melting point 93°–95° C.

Compound 7

4,5-Dichloro-3-(2,6-dichloro-phenylimino)-1,2-dithiolene; melting point: 106°–110° C.

Compound 8

4,5-Dichloro-3-(2,3-dichloro-phenylimino)-1,2-dithiolene; melting point: 99°–102° C.

EXAMPLE 7 (Compound 9)

4,5-Dichloro-3-(2,4-dimethyl-phenylimino)-1,2-dithiolene 14.0 g of 2,4-dimethyl-aniline were dissolved in 300 ml of methylene chloride and 50 ml of triethylamine and 31.0 g of 3,4,5-trichloro-1,2-dithiolium chloride were introduced at 10°–15° C. After stirring for three hours at 20° C., a test for aromatic amine, by diazotizing and coupling, proved negative. The resulting dark solution was then washed three times with 200 ml of water, dried over potassium carbonate and filtered over a column of aluminum oxide, to remove impurities that imparted a color. The filtrate was concentrated and caused to crystallize by adding petroleum ether. Yield, 17.0 g of yellowish crystals; melting point: 72°–74° C. The elementary analysis and NMR spectrum agreed with the assumed structure.

The following were obtained analogously:

Compound 10

4,5-Dichloro-3-(2-chloro-phenylimino)-1,2-dithiolene; melting point: 77°–78° C.

Compound 11

4,5-Dichloro-3-(2,6-diethyl-phenylimino)-1,2-dithiolene; (viscous oil).

Compound 12

4,5-Dichloro-3-(2,6-diisopropyl-phenylimino)-1,2-dithiolene; melting point: 112°–115° C.

Compound 13

4,5-Dichloro-3-(2,5-dimethoxy-phenylimino)-1,2-dithiolene; melting point: 175° C., with decomposition.

Compound 14

4,5-Dichloro-3-(3-trifluoromethyl-phenylimino)-1,2-dithiolene; melting point: 45°–48° C.

Compound 15

N,N'-Bis-(4,5-dichloro-1,2-dithiolen-3-ylidene)-1,4-phenylene-diamine

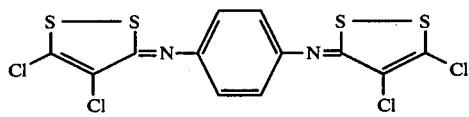

10.0 g of 1,4-phenylenediamine were dissolved in 300 ml of methylene chloride and 80 ml of triethylamine and 51.0 g of 3,4,5-trichloro-1,2-dithiolium chloride were introduced at 10°–15° C. The mixture was stirred for 12 hours at 20° C. and the dark batch was washed twice with a mixture of 300 ml of water and 20 ml of acetic acid. Insoluble matter was then filtered off and rinsed with methylene chloride; yield 35.0 g; a second fraction was obtained by concentrating the dried methylene chloride phase. Purification could be effected by continuous extraction in a Soxhlet apparatus; yellowish crystals, melting point above 300° C.

It will be appreciated that the instant specification and examples are set forth by way of illustration and not limitation, and that various modifications and changes may be made without departing from the spirit and scope of the present invention.

What is claimed is:

1. A compound selected from the group consisting of

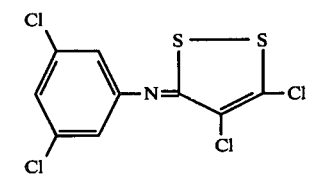

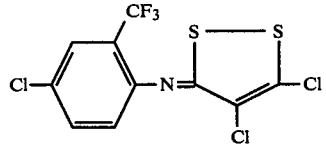

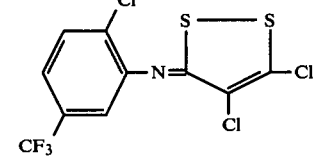

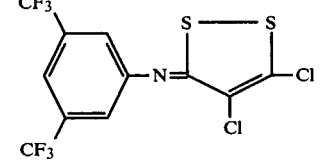

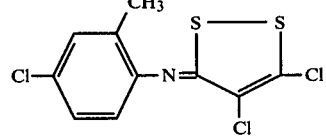

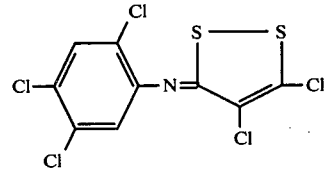

-continued

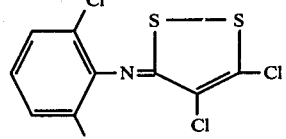

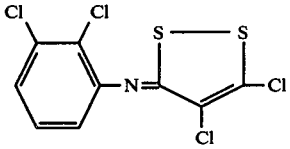

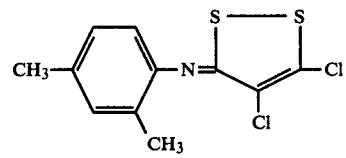

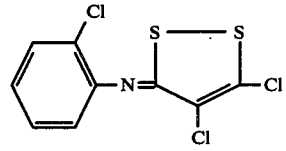

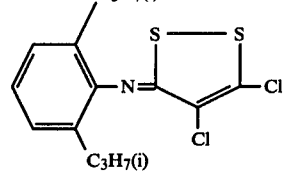

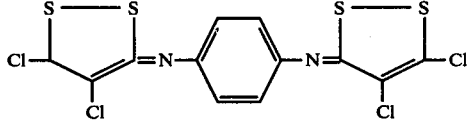

and

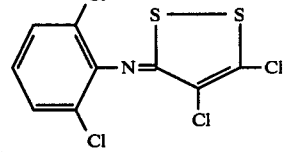

2. A compound according to claim 1 wherein such compound is

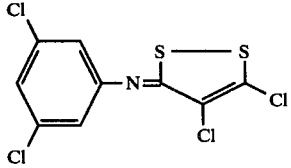

3. A compound according to claim 1 wherein such compound is

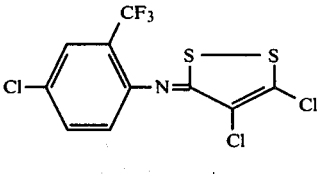

4. A compound according to claim 1 wherein such compound is

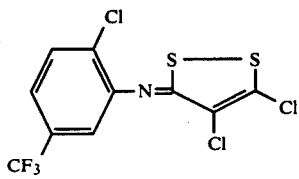

5. A compound according to claim 1 wherein such compound is

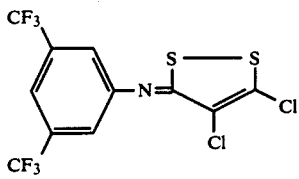

6. A compound according to claim 1 wherein such compound is

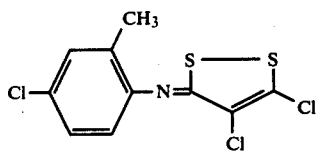

7. A compound according to claim 1 wherein such compound is

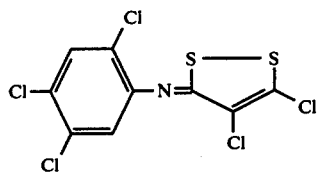

8. A compound according to claim 1 wherein such compound is

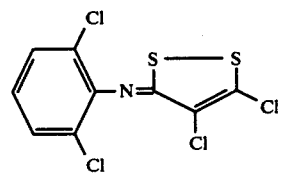

9. A compound according to claim 1 wherein such compound is

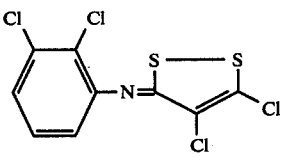

10. A compound according to claim 1 wherein such compound is

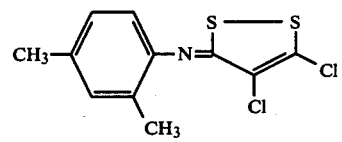

11. A compound according to claim 1 wherein such compound is

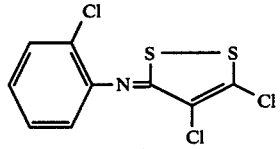

12. A compound according to claim 1 wherein such compound is

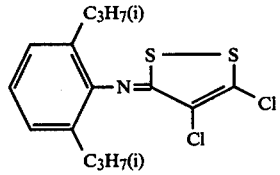

13. A compound according to claim 1 wherein such compound is

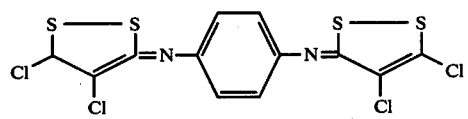

14. An arthropodicidal, nematicidal or fungicidal composition containing as active ingredient an arthropodicidally, nematicidally or fungicidally effective amount of a compound according to claim 1 in admixture with a diluent.

15. A method of combating arthropods, nematodes or fungi which comprises applying to the arthropods, nematodes or fungi, or to a habitat thereof, an arthropodicidally, nematicidally or fungicidally effective amount of a compound according to claim 1.

* * * * *